(12) United States Patent
Nagaoka et al.

(10) Patent No.: US 10,709,886 B2
(45) Date of Patent: Jul. 14, 2020

(54) ELECTRICAL STIMULATION LEADS AND SYSTEMS WITH ELONGATE ANCHORING ELEMENTS AND METHODS OF MAKING AND USING

(71) Applicant: Boston Scientific Neuromodulation Corporation, Valencia, CA (US)

(72) Inventors: Eric Koji Nagaoka, Camarillo, CA (US); Jacob B. Leven, Huntington Beach, CA (US); Abraham Molina Ortega, San Fernando, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 167 days.

(21) Appl. No.: 15/905,398

(22) Filed: Feb. 26, 2018

(65) Prior Publication Data

US 2018/0243551 A1     Aug. 30, 2018

Related U.S. Application Data

(60) Provisional application No. 62/464,902, filed on Feb. 28, 2017.

(51) Int. Cl.
*A61N 1/00* (2006.01)
*A61N 1/05* (2006.01)
(Continued)

(52) U.S. Cl.
CPC .............. *A61N 1/05* (2013.01); *A61N 1/057* (2013.01); *A61N 1/059* (2013.01); *A61N 1/0558* (2013.01);
(Continued)

(58) Field of Classification Search
CPC ........ A61N 1/05; A61N 1/0558; A61N 1/059; A61N 1/057; A61N 1/37217; A61N 1/3787
See application file for complete search history.

(56) References Cited

U.S. PATENT DOCUMENTS 376,810 A    1/1888  Brill
612,685 A   10/1898  Thorp et al.
(Continued)

FOREIGN PATENT DOCUMENTS

AU    2012201634       4/2012
EP          85417 A1   8/1983
(Continued)

*Primary Examiner* — Scott M. Getzow
(74) *Attorney, Agent, or Firm* — Lowe Graham Jones PLLC; Bruce E. Black

(57) ABSTRACT

An electrical stimulation lead includes a body having distal and proximal end portions, a longitudinal length, at least one anchoring lumen, and at least one open slot spaced apart from each end of the lead body. Each anchoring lumen is open at a slot and extends both distally and proximally from the slot. The lead also includes electrodes; terminals; conductors electrically coupling the terminals to the electrodes; and at least one anchoring element at least partially disposed in an anchoring lumen. Each anchoring element includes at least one bent portion biased to extend an extension portion of the anchoring element out of a slot when the anchoring element is in a deployed position and can retract the extension portion into an anchoring lumen when the anchoring element is in a constrained position. The lead further includes an attachment member attached to each anchoring element and disposed proximal to each slot.

19 Claims, 13 Drawing Sheets

(51) Int. Cl.
*A61N 1/378* (2006.01)
*A61N 1/372* (2006.01)

(52) U.S. Cl.
CPC ........ *A61N 1/3787* (2013.01); *A61N 1/37217* (2013.01)

(56) References Cited

U.S. PATENT DOCUMENTS

| | | |
|---|---|---|
| 2,046,837 A | 7/1936 | Phillips |
| 3,333,045 A | 7/1967 | Fisher et al. |
| 3,866,615 A | 2/1975 | Hewson |
| 3,918,440 A | 11/1975 | Kraus |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,143,090 A | 9/1992 | Dutcher et al. |
| 5,158,097 A | 10/1992 | Christlieb |
| 5,217,028 A | 6/1993 | Dutcher et al. |
| 5,228,248 A | 7/1993 | Haddock |
| 5,269,809 A | 12/1993 | Hayhurst et al. |
| 5,330,477 A | 7/1994 | Crook |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,738,521 A | 4/1998 | Dugot |
| 5,746,722 A | 5/1998 | Pohndorf et al. |
| 5,865,843 A | 2/1999 | Baudino |
| 5,876,431 A | 3/1999 | Spehr et al. |
| 5,895,360 A | 4/1999 | Christopherson et al. |
| 5,957,968 A | 9/1999 | Belden et al. |
| 6,104,957 A | 8/2000 | Alo et al. |
| 6,175,710 B1 | 1/2001 | Kamaji et al. |
| 6,181,969 B1 | 1/2001 | Gord |
| 6,192,279 B1 | 2/2001 | Barreras, Sr. et al. |
| 6,224,450 B1 | 5/2001 | Norton |
| 6,271,094 B1 | 8/2001 | Boyd et al. |
| 6,295,944 B1 | 10/2001 | Lovett |
| 6,360,750 B1 | 3/2002 | Gerber et al. |
| 6,364,278 B1 | 4/2002 | Lin et al. |
| 6,391,985 B1 | 5/2002 | Goode et al. |
| 6,473,654 B1 | 10/2002 | Chinn |
| 6,506,190 B1 | 1/2003 | Walshe |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,902,547 B2 | 6/2005 | Aves et al. |
| 6,978,180 B2 | 12/2005 | Tadlock |
| 6,984,145 B1 | 1/2006 | Lim |
| 7,056,333 B2 | 6/2006 | Walshe |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,203,548 B2 | 4/2007 | Whitehurst et al. |
| 7,235,078 B2 | 7/2007 | West, Jr. |
| 7,244,150 B1 | 7/2007 | Brase et al. |
| 7,337,005 B2 | 2/2008 | Kim et al. |
| 7,337,006 B2 | 2/2008 | Kim et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,450,993 B2 | 11/2008 | Kim et al. |
| 7,450,997 B1 | 11/2008 | Pianca et al. |
| 7,502,651 B2 | 3/2009 | Kim et al. |
| 7,580,753 B2 | 8/2009 | Kim et al. |
| 7,596,414 B2 | 9/2009 | Whitehurst et al. |
| 7,610,102 B2 | 10/2009 | Kowalczyk |
| 7,610,103 B2 | 10/2009 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,787,960 B2 | 8/2010 | Lubenow |
| 7,792,590 B1 | 9/2010 | Pianca et al. |
| 7,809,446 B2 | 10/2010 | Meadows |
| 7,848,803 B1 | 12/2010 | Jaax et al. |
| 7,853,321 B2 | 12/2010 | Jaax et al. |
| 7,860,568 B2 | 12/2010 | Deininger et al. |
| 7,949,395 B2 | 5/2011 | Kuzma |
| 7,974,706 B2 | 7/2011 | Moffitt et al. |
| 7,993,378 B2 | 8/2011 | Foley et al. |
| 8,019,443 B2 | 9/2011 | Schleicher et al. |
| 8,082,039 B2 | 12/2011 | Kim et al. |
| 8,175,710 B2 | 5/2012 | He |
| 8,204,595 B2 | 6/2012 | Pianca et al. |
| 8,224,450 B2 | 7/2012 | Brase |
| 8,224,451 B2 | 7/2012 | Jaax et al. |
| 8,229,565 B2 | 7/2012 | Kim et al. |
| 8,229,573 B2 | 7/2012 | Chen et al. |
| 8,271,094 B1 | 9/2012 | Moffitt et al. |
| 8,295,944 B2 | 10/2012 | Howard et al. |
| 8,315,704 B2 | 11/2012 | Jaax et al. |
| 8,364,278 B2 | 1/2013 | Pianca et al. |
| 8,391,985 B2 | 3/2013 | McDonald |
| 8,483,237 B2 | 7/2013 | Zimmerman et al. |
| 8,568,462 B2 | 10/2013 | Sixto et al. |
| 8,647,346 B2 | 2/2014 | Bleich et al. |
| 8,688,232 B2 | 4/2014 | Finley et al. |
| 8,688,235 B1 | 4/2014 | Pianca et al. |
| 8,712,546 B2 | 4/2014 | Kim et al. |
| 8,718,790 B2 | 5/2014 | Pianca |
| 8,768,488 B2 | 7/2014 | Barker |
| 8,774,926 B2 | 7/2014 | Alataris et al. |
| 8,781,603 B2 | 7/2014 | Ye et al. |
| 8,831,742 B2 | 9/2014 | Pianca et al. |
| 8,849,422 B2 | 9/2014 | Pianca |
| 8,897,893 B2 | 11/2014 | Pianca |
| 8,983,624 B2 | 3/2015 | Imran |
| 9,089,694 B2 | 7/2015 | Pianca |
| 9,138,574 B2 | 9/2015 | Kern et al. |
| 9,199,074 B2 | 12/2015 | Pianca |
| 9,205,259 B2 | 12/2015 | Kim et al. |
| 9,205,260 B2 | 12/2015 | Kim et al. |
| 9,259,569 B2 | 2/2016 | Brounstein et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033374 A1 | 2/2005 | Gerber |
| 2005/0033393 A1 | 2/2005 | Daglow |
| 2005/0165465 A1 | 7/2005 | Pianca et al. |
| 2005/0240238 A1 | 10/2005 | Mamo et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0112385 A1 | 5/2007 | Conlon |
| 2007/0150036 A1 | 6/2007 | Anderson |
| 2007/0219595 A1 | 9/2007 | He |
| 2007/0239248 A1 | 10/2007 | Hastings et al. |
| 2007/0255369 A1 | 11/2007 | Bonde et al. |
| 2007/0265682 A1 | 11/2007 | Wiegnann et al. |

(56) References Cited

U.S. PATENT DOCUMENTS

| | | |
|---|---|---|
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0196939 A1 | 8/2008 | Lubenow et al. |
| 2008/0228251 A1 | 9/2008 | Hill |
| 2008/0243220 A1 | 10/2008 | Barker |
| 2008/0262588 A1 | 10/2008 | Zarembo et al. |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0187222 A1 | 7/2009 | Barker |
| 2009/0198312 A1 | 8/2009 | Barker |
| 2009/0204193 A1 | 8/2009 | Kokones et al. |
| 2009/0210043 A1 | 8/2009 | Reddy |
| 2009/0248095 A1 | 10/2009 | Schleicher et al. |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0276021 A1 | 11/2009 | Meadows et al. |
| 2009/0276025 A1 | 11/2009 | Burnes et al. |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0076535 A1 | 3/2010 | Pianca et al. |
| 2010/0094425 A1 | 4/2010 | Bentley et al. |
| 2010/0137938 A1 | 6/2010 | Kishawi et al. |
| 2010/0174240 A1 | 7/2010 | Wells et al. |
| 2010/0179562 A1 | 7/2010 | Linker et al. |
| 2010/0241179 A1 | 9/2010 | Gielen et al. |
| 2010/0249875 A1 | 9/2010 | Kishawi et al. |
| 2010/0268298 A1 | 10/2010 | Moffitt et al. |
| 2010/0274336 A1 | 10/2010 | Nguyen-Stella et al. |
| 2010/0286670 A1 | 11/2010 | Doyle et al. |
| 2010/0312319 A1 | 12/2010 | Barker |
| 2011/0004267 A1 | 1/2011 | Meadows |
| 2011/0005069 A1 | 1/2011 | Pianca |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0213445 A1 | 9/2011 | Blischak |
| 2011/0238129 A1 | 9/2011 | Moffitt et al. |
| 2011/0264180 A1 | 10/2011 | Hamilton |
| 2011/0276056 A1 | 11/2011 | Grigsby et al. |
| 2011/0313427 A1 | 12/2011 | Gindele et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0101326 A1 | 4/2012 | Simon et al. |
| 2012/0150202 A1 | 6/2012 | Chen et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232626 A1 | 9/2012 | Daglow |
| 2012/0277670 A1 | 11/2012 | Goetz |
| 2012/0283835 A1 | 11/2012 | Bentley et al. |
| 2012/0316615 A1 | 12/2012 | Digiore et al. |
| 2012/0316627 A1* | 12/2012 | Finlay ............... A61N 1/0512 607/116 |
| 2012/0323253 A1* | 12/2012 | Garai ............... A61N 1/057 606/129 |
| 2012/0330355 A1 | 12/2012 | Finley et al. |
| 2013/0096659 A1 | 4/2013 | Ranu |
| 2013/0105071 A1 | 5/2013 | Digiore et al. |
| 2013/0149031 A1 | 6/2013 | Changsrivong |
| 2013/0197424 A1 | 8/2013 | Bedenbaugh |
| 2013/0197602 A1 | 8/2013 | Pianca et al. |
| 2013/0204336 A1 | 8/2013 | Sharma |
| 2013/0238023 A1 | 9/2013 | Wales et al. |
| 2013/0261684 A1 | 10/2013 | Howard |
| 2013/0317518 A1 | 11/2013 | Govea |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2013/0325091 A1 | 12/2013 | Pianca et al. |
| 2014/0018885 A1 | 1/2014 | Pianca |
| 2014/0039587 A1 | 2/2014 | Romero |
| 2014/0074093 A9 | 3/2014 | Nelson et al. |
| 2014/0180345 A1 | 6/2014 | Chan et al. |
| 2014/0257240 A1 | 9/2014 | Burdulis |
| 2014/0276925 A1 | 9/2014 | Alves et al. |
| 2014/0296953 A1 | 10/2014 | Pianca et al. |
| 2014/0343645 A1 | 11/2014 | Wechter |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0005856 A1 | 1/2015 | Pianca et al. |
| 2015/0018915 A1 | 1/2015 | Leven |
| 2015/0021817 A1 | 1/2015 | Romero et al. |
| 2015/0045864 A1 | 2/2015 | Howard |
| 2015/0045865 A1 | 2/2015 | Nageri et al. |
| 2015/0051674 A1 | 2/2015 | Barner et al. |
| 2015/0051675 A1 | 2/2015 | Barner |
| 2015/0066120 A1 | 3/2015 | Govea |
| 2015/0066121 A1 | 3/2015 | Govea et al. |
| 2015/0099936 A1 | 4/2015 | Burdulis et al. |
| 2015/0134038 A1* | 5/2015 | Spinelli ............... A61N 1/0551 607/116 |
| 2015/0151113 A1 | 6/2015 | Govea et al. |
| 2015/0246216 A1 | 9/2015 | Barker |
| 2015/0343198 A1 | 12/2015 | Nageri et al. |
| 2017/0036013 A1 | 2/2017 | Leven |
| 2017/0202616 A1* | 7/2017 | Pate ............... A61B 6/487 |
| 2017/0246454 A1 | 8/2017 | Leven |
| 2017/0333702 A1 | 11/2017 | Barner |
| 2018/0021569 A1 | 1/2018 | Pianca |

FOREIGN PATENT DOCUMENTS

| | | |
|---|---|---|
| EP | 0597213 A1 | 5/1994 |
| JP | H07-014681 | 3/1995 |
| JP | 2001339829 A | 12/2001 |
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2003020365 | 3/2003 |
| WO | 2003084398 | 10/2003 |
| WO | 2004/054655 | 7/2004 |
| WO | 2005120203 | 12/2005 |
| WO | 2006029257 | 3/2006 |
| WO | 2006/086363 A2 | 8/2006 |
| WO | 2007041604 | 4/2007 |
| WO | 2007/056384 A2 | 5/2007 |
| WO | 2007/083108 A2 | 7/2007 |
| WO | 2007/149994 A2 | 12/2007 |
| WO | 2008/09789 A1 | 8/2008 |
| WO | 2008101026 A1 | 8/2008 |
| WO | 2008/121708 A2 | 10/2008 |
| WO | 2010083308 | 7/2010 |
| WO | 2010/126853 A1 | 11/2010 |
| WO | 2012151356 A1 | 11/2012 |
| WO | 2013112920 A1 | 8/2013 |

* cited by examiner

ELECTRICAL STIMULATION LEADS AND SYSTEMS WITH ELONGATE ANCHORING ELEMENTS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/464,902, filed Feb. 28, 2017, which is incorporated herein by reference.

FIELD

The present invention is directed to the area of implantable electrical stimulation systems and methods of making and using the systems, and in particular implantable electrical stimulation leads having elongate anchoring elements and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead that includes a lead body having a distal end portion, a proximal end portion, a longitudinal length; electrodes disposed along the distal end portion of the lead body; terminals disposed along the proximal end portion of the lead body; and conductors electrically coupling the plurality of terminals to the plurality of electrodes. The lead body includes at least one anchoring lumen that extends longitudinally along at least a portion of the lead body. The lead body also includes at least one open slot that is spaced apart from each end of the lead body. Each of the at least one anchoring lumen is open at one of the at least one open slot and extends both distally and proximally from the one of the at least one open slot. The electrical stimulation lead also includes at least one anchoring element at least partially disposed in one of the at least one anchoring lumen. Each of the at least one anchoring element includes at least one bent portion. Each of the at least one bent portion is biased to extend an extension portion of the anchoring element out of one of the at least one slot when the anchoring element is in a deployed position and can retract the extension portion into the respective anchoring lumen when the anchoring element is in a constrained position. The electrical stimulation lead additionally includes an attachment member attached to each of the at least one anchoring element. The attachment member is disposed proximal to each of the at least one slot.

In at least some embodiments, the attachment member is a band disposed along the lead body. In at least some embodiments, the lead body has an outer diameter that exceeds an inner diameter of the band. In at least some embodiments, the band has an outer diameter that exceeds an outer diameter of the lead body.

In at least some embodiments, the attachment member includes at least two separate attachment members and the at least one anchoring element comprises a plurality of anchoring elements, each of the at least two separate attachment members being attached to different ones of the anchoring elements. In at least some embodiments, the at least one anchoring element includes a plurality of anchoring elements, the anchoring elements being spaced apart from each other around the lead. In at least some embodiments, the anchoring elements are uniformly spaced apart from each other around the lead. In at least some embodiments, the anchoring elements are non-uniformly spaced apart from each other around the lead. In at least some embodiments, the extension portions of at last two of the anchoring elements have different shapes.

In at least some embodiments, when the extension portion of one of the at least one anchoring element extends out of the slot associated with the anchoring element, the extension portion forms two sides of a triangular shape that extends away from the lead body. In at least some embodiments, the two sides of the triangular shape include a distal side and a proximal side, the proximal side being shorter than the distal side. In at least some embodiments, the proximal side is longer than the distal side. In at least some embodiments, when the extension portion of one of the at least one anchoring element extends out of the slot associated with the one anchoring element, the extension portion has an arc shape.

In at least some embodiments, each of the at least one anchoring element is attached to at least one of the plurality of electrodes. In at least some embodiments, the attachment member and the at least one anchoring element are attached to each other by at least one welding joint.

Another embodiment is an electrical stimulating system that includes any of the electrical stimulation leads described above; and a control module coupleable to the electrical stimulation lead.

A further embodiment is a method of implanting any of the electrical stimulation leads described above. The method includes sliding an introducer over the lead body to push each of the at least one anchoring element through the slot associated with the anchoring element into the constrained position in the anchoring lumen in which the anchoring element is disposed; implanting the electrical stimulation lead into tissue of a patient while the introducer constrains each of the at least one anchoring element in the constrained position; and removing the introducer to extend each of the at least one anchoring element from the constrained position to the deployed position in the tissue of the patient.

An additional embodiment is a method of explanting any of the electrical stimulation leads described above. The method includes pulling the attachment member in a direction away from the at least one slot, thereby retracting each extension portion of each of the at least one anchoring element through the slot associated with the anchoring element into the anchoring lumen in which the anchoring element is disposed; and explanting the lead body from tissue of a patient after pulling the attachment member.

In at least some embodiments, prior to pulling the attachment member, the lead body is cut proximal to the one attachment member so that the attachment member can be disengaged from the lead body. In at least some embodiments, while pulling the attachment member, a portion of the lead body distal to the attachment member is compressed.

In at least some embodiments, pulling the attachment member in the direction away from the at least one slot includes completely removing each of the at least one anchoring element from the lead body.

In at least some embodiments, explanting the lead body from the tissue of the patient after pulling the attachment member includes explanting the lead body from the tissue of the patient while each of the at least one anchoring element is at least partially disposed in the lead body in a restrained position and each extension portion of each of the at least one anchoring element is retracted into the anchoring lumen in which the anchoring element is disposed.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems, and in particular implantable electrical stimulation leads having elongate anchoring elements and methods of making and using the leads.

Suitable implantable electrical stimulation systems include, but are not limited to, a least one lead with at least one electrode disposed along a distal end of the lead and at least one terminal disposed along the at least one proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1:
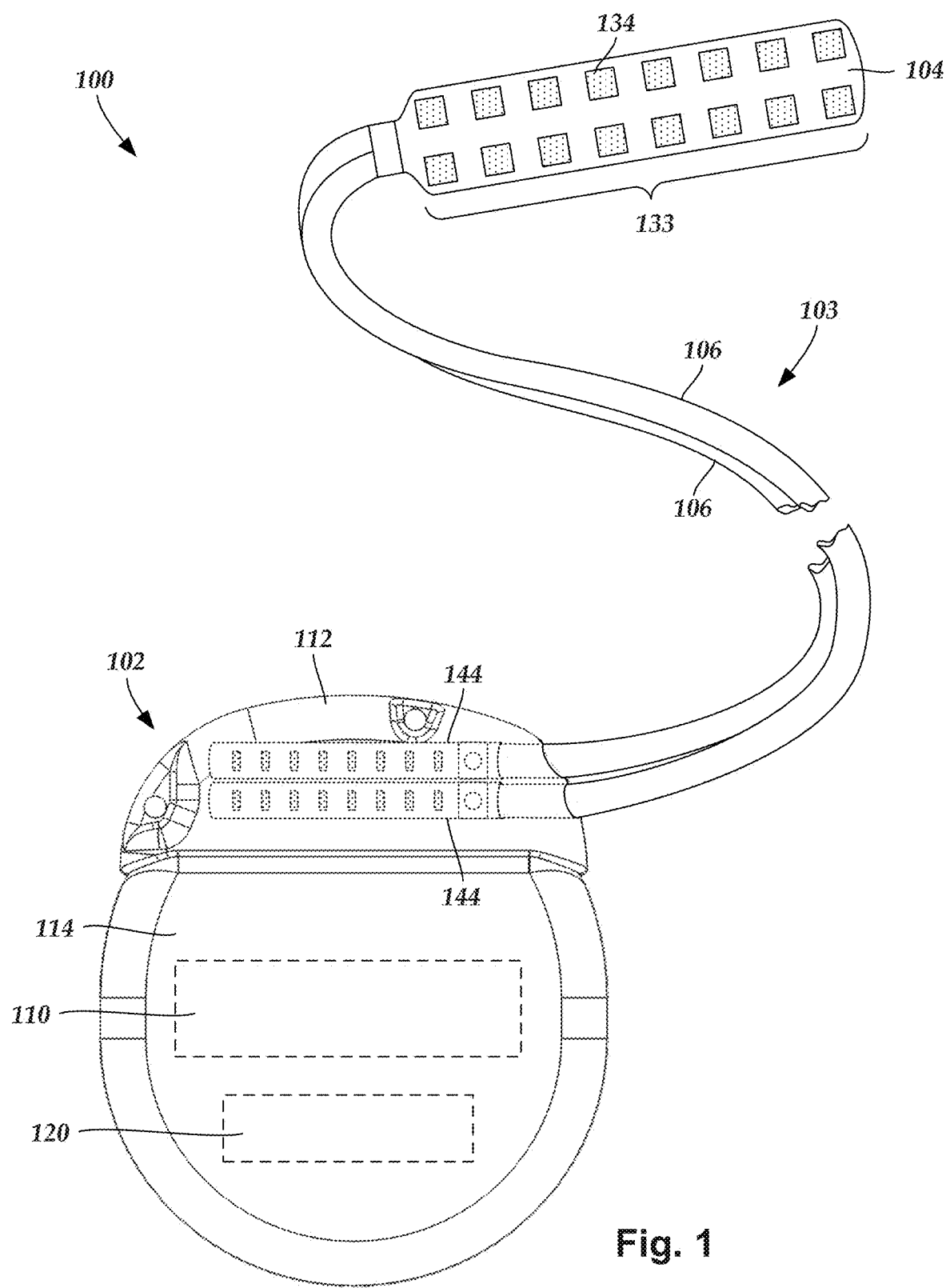
FIG. 1 is a schematic front view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (for example, a stimulator or pulse generator) 102 and a lead 103 coupleable to the control module 102. The lead 103 includes a paddle body 104 and at least one lead body 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (for example, 310 in FIG. 3A) is disposed along each of the at least one lead body 106. In at least some embodiments, there may be a single electrode 134 or a single terminal.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
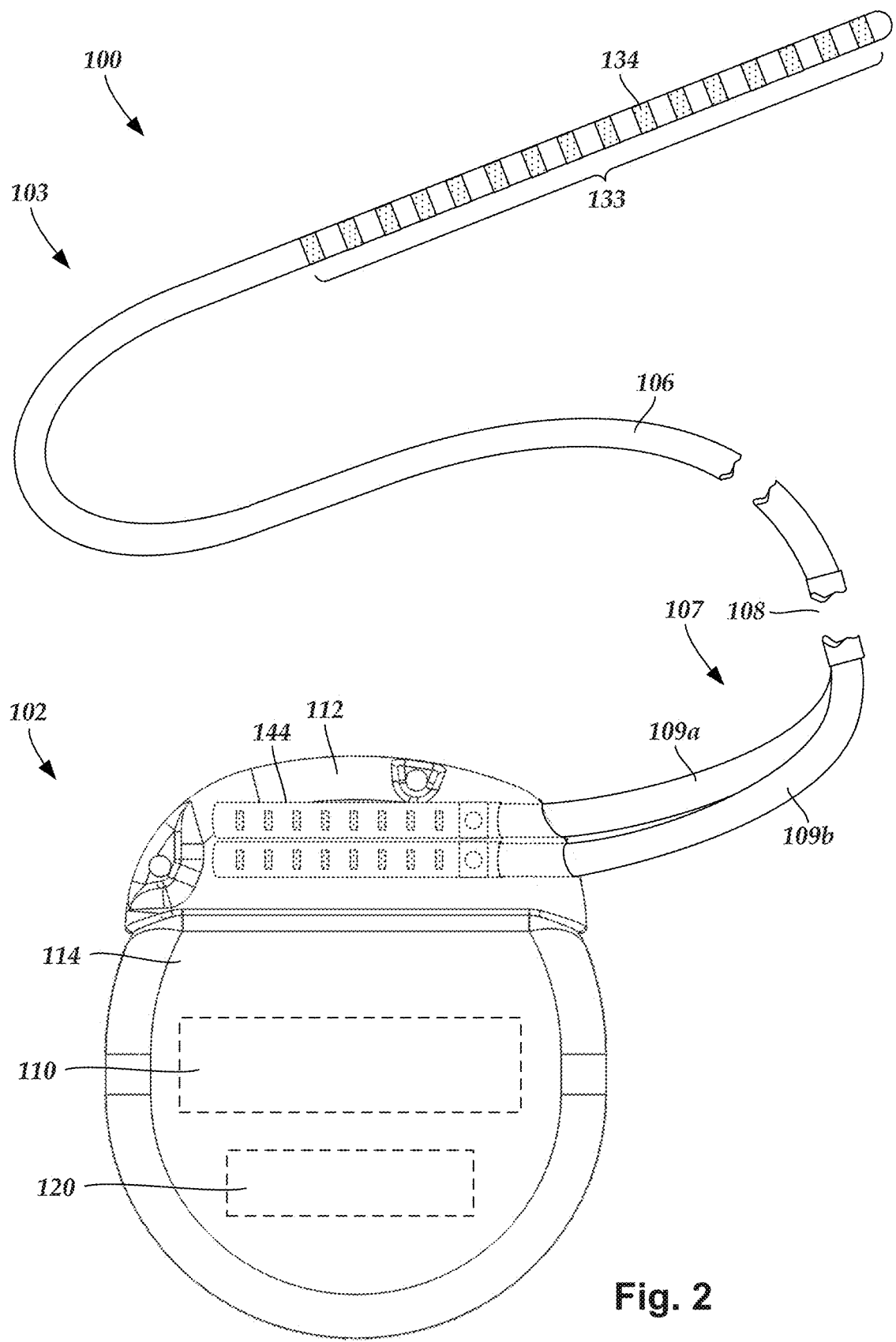
FIG. 2 is a schematic front view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the at least one lead body 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via at least one intermediate device (324 in FIG. 3B). For example, in at least some embodiments at least one lead extension 324 (see, for example, FIG. 3B) can be disposed between the lead 103 and the control module 102 to extend the distance between the lead 103 and the control module 102. Other intermediate devices may be used in addition to, or in lieu of, at least one lead extension including, for example, a splitter, an adaptor, or the like or combinations thereof. It will be understood that, in the case where the electrical stimulation system 100 includes multiple intermediate devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and at least one splitter tail 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system 100 or components of the electrical stimulation system 100, including the paddle body 104, the at least one of the lead bodies 106, and the control module 102, are typically implanted into the body of a patient. The electrical stimulation system 100 can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, at least one of the electrodes 134 are formed from at least one of: platinum, platinum iridium, palladium, palladium rhodium, or titanium.

Any suitable number of electrodes 134 can be disposed on the lead 103 including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes 134 of the paddle body 104 (or at least one lead body 106) are typically disposed in, or separated by, a non-conductive, biocompatible material such as, for example, silicone, polyurethane, polyetheretherketone ("PEEK"), epoxy, and the like or combinations thereof. The at least one lead body 106 and, if applicable, the paddle body 104 may be formed in the desired shape by any process including, for example, molding (including injection molding), casting, and the like. The non-conductive material typically extends from the distal ends of the at least one lead body 106 to the proximal end of each of the at least one lead body 106.

In the case of paddle leads, the non-conductive material typically extends from the paddle body 104 to the proximal end of each of the at least one lead body 106. Additionally, the non-conductive, biocompatible material of the paddle body 104 and the at least one lead body 106 may be the same or different. Moreover, the paddle body 104 and the at least one lead body 106 may be a unitary structure or can be formed as two separate structures that are permanently or detachably coupled together.

Figure 3A:
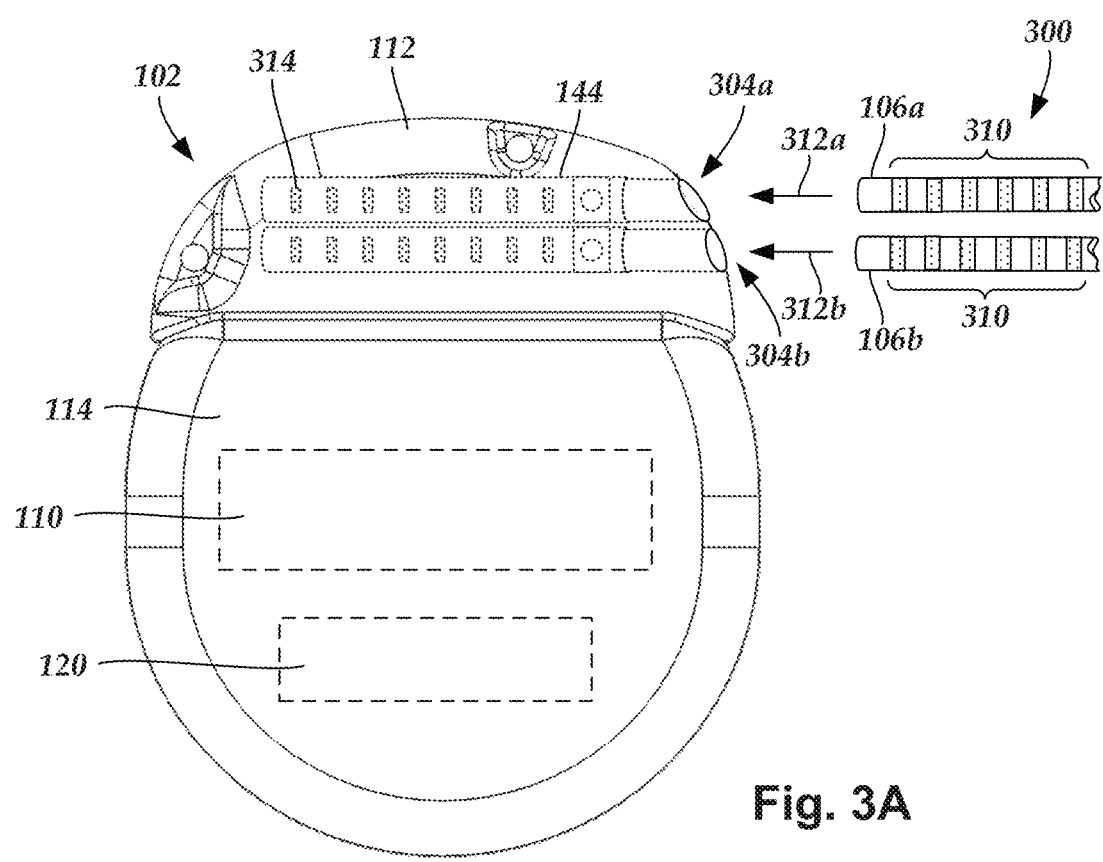
FIG. 3A is a schematic front view of one embodiment of the control module of FIG. 1 configured and arranged to electrically couple to a lead body, according to the invention.

Terminals (for example, 310 in FIG. 3A) are typically disposed along the proximal end of the at least one lead body 106 of the electrical stimulation system 100 (as well as any splitters, lead extensions, adaptors, or the like) for electrical connection to corresponding connector contacts (for example, 314 in FIG. 3A). The connector contacts are disposed in connectors (for example, 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, at least one electrode 134 are electrically coupled to each terminal. In at least some embodiments, each terminal is only connected to one electrode 134.

The electrically conductive wires ("conductors") may be embedded in the non-conductive material of the lead body 106 or can be disposed in at least one lumen (see, for example, FIGS. 4F and 4G) extending along the lead body 106. In at least some embodiments, there is an individual lumen for each conductor. In other embodiments, two or more conductors extend through a lumen. There may also be at least one lumen (see, for example, FIGS. 4F and 4G) that open at, or near, the proximal end of the at least one lead body 106, for example, for inserting a stylet to facilitate placement of the at least one lead body 106 within a body of a patient. Additionally, there may be at least one lumen (see, for example, FIGS. 4F and 4G) that open at, or near, the distal end of the at least one lead body 106, for example, for infusion of drugs or medication into the site of implantation of the at least one lead body 106. In at least some embodiments, the at least one lumen are flushed continually, or on a regular basis, with saline, epidural fluid, or the like. In at least some embodiments, the at least one lumen are permanently or removably sealable at the distal end.

FIG. 3A is a schematic side view of one embodiment of a proximal end of at least one elongated device 300 configured and arranged for coupling to one embodiment of the control module connector 144. The at least one elongated device 300 may include, for example, at least one of the lead bodies 106 of FIG. 1, at least one intermediate device (for example, a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3A (and in other figures), the connector housing 112 is shown having two ports 304*a* and 304*b*. The connector housing 112 can define any suitable number of ports including, for example, one, two, three, four, five, six, seven, eight, or more ports.

The control module connector 144 also includes a plurality of connector contacts, such as connector contact 314, disposed within each port 304*a* and 304*b*. When the elongated device 300 is inserted into the ports 304*a* and 304*b*, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
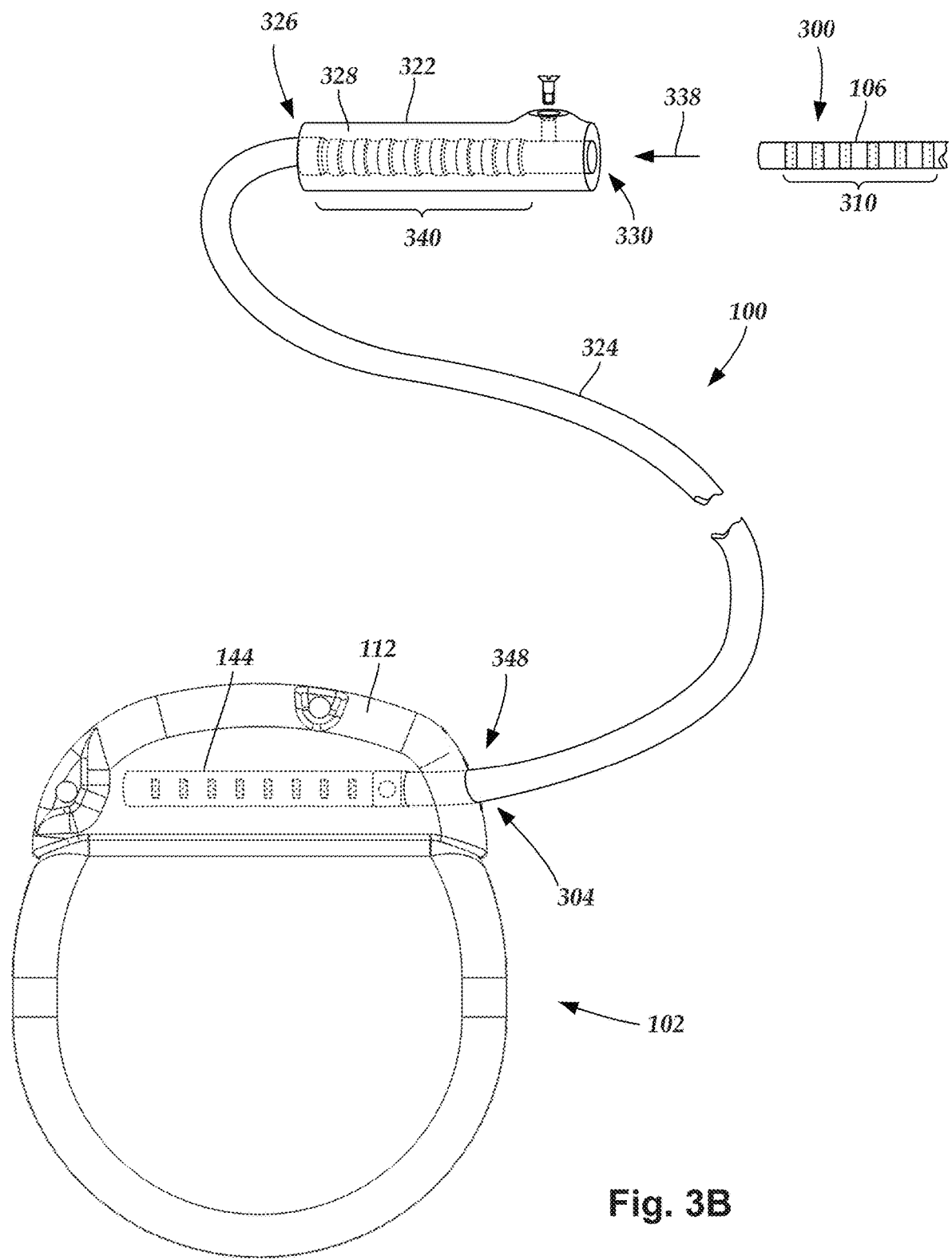
FIG. 3B is a schematic front view of one embodiment of a lead extension configured and arranged to electrically couple a lead body to a control module, according to the invention.

FIG. 3B is a schematic side view of another embodiment of the electrical stimulation system 100. The electrical stimulation system 100 includes a lead extension 324 that is configured and arranged to couple at least one elongated device 300 (for example, one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Lead anchoring elements can be attached to the lead to facilitate anchoring the lead into patient tissue. The term "tissue" includes, but is not limited to, muscular tissue, connective tissue, organ tissue, bone, cartilage, nerve tissue, and the like. These lead anchoring elements, as opposed to conventional lead anchors, can be delivered with the lead through an introducer during the implantation process. The lead anchoring elements extend into, and lodge against, patient tissue and prevent or reduce lateral or axial (or both lateral and axial) migration of the lead after implantation. The lead anchoring elements can be particularly useful for leads for sacral nerve stimulation, spinal cord stimulation, or the stimulation of other patient tissue and organs. Although the anchoring elements are discussed below for use with a lead, it will be understood that the same anchoring elements can be used with a lead extension. Moreover, where the discussion below describes electrodes of the lead, the corresponding element in a lead extension would be the connector or connector contacts of the lead extension.

Figure 4A:
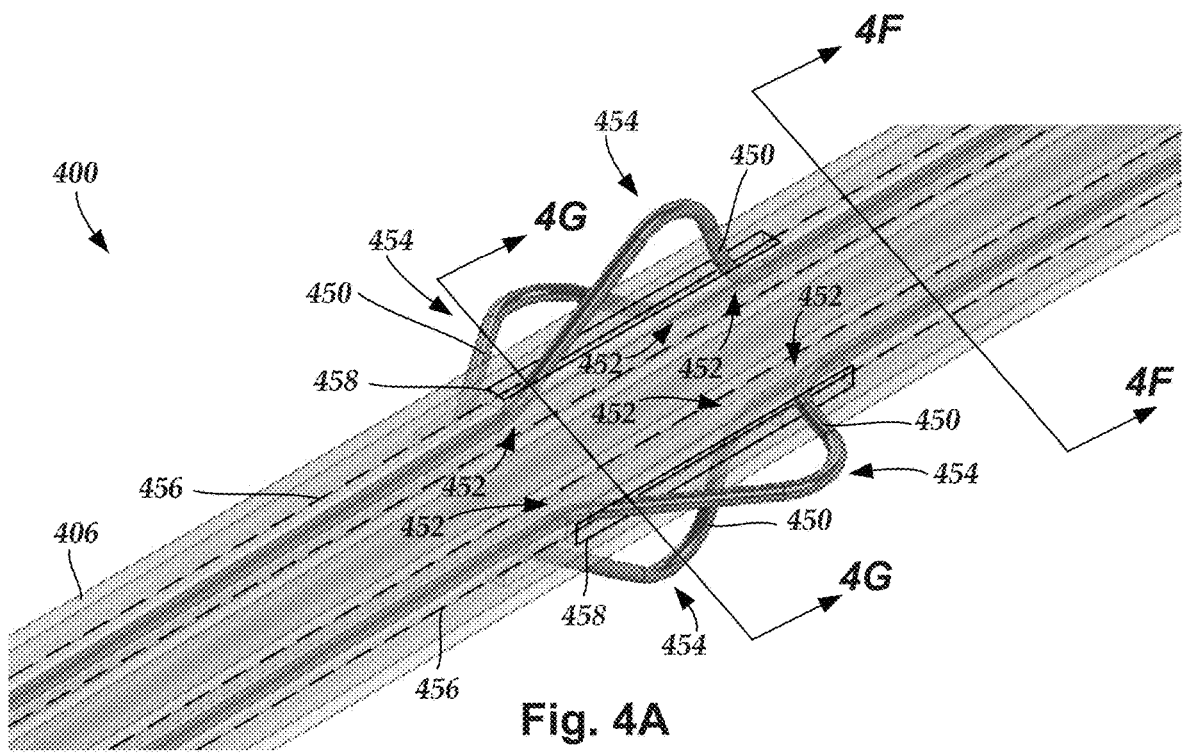
FIG. 4A is a schematic perspective view of a portion of one embodiment of a multi-lumen guide of a lead with anchoring elements, according to the invention.

FIG. 4A illustrates one embodiment of a portion of a lead 400 with a lead body 406 (illustrated as partially transparent to show the interior of the lead body 406) and anchoring elements 450 disposed in anchoring lumens 456. The anchoring lumens 456 extend inside the lead body 406 and each anchoring lumen includes at least one open slot 458 through the lead body to expose a portion of the anchoring lumen. Each anchoring element 450 includes at least one bent portion 452. In at least some embodiments, the bent portion 452 is biased to extend at least partially out of a slot 458 of the anchoring lumen 456 in which the anchoring element 458 resides (for example, extending at least 0.1, 0.2, 0.3, 0.4, or 0.5 mm from the lead body 406). This is a deployed position of the anchoring element 458 with an extension portion 454 disposed outside of the lead body 406. Although the illustrated embodiment shows one slot 458 and extension portion 454 per anchoring element 450, each anchoring element 450 may have multiple extension portions 454 that, in the deployed position, extend through multiple slots 458 (for example, longitudinally or circumferentially offset extension portions 454 and slots 458).

Figure 4B:
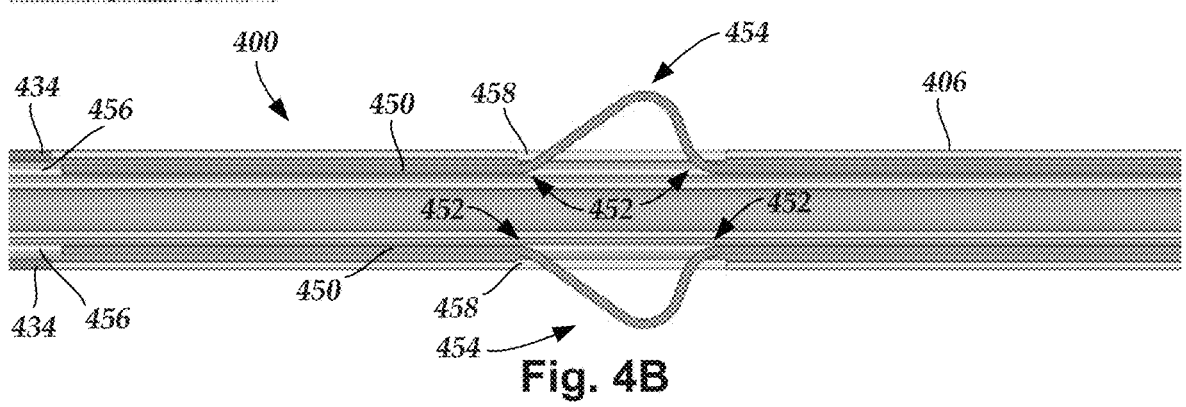
FIG. 4B is a schematic longitudinal cross-sectional view of one embodiment of the multi-lumen guide of the lead of FIG. 4A with the anchoring elements in a deployed position, according to the invention.
Figure 4C:
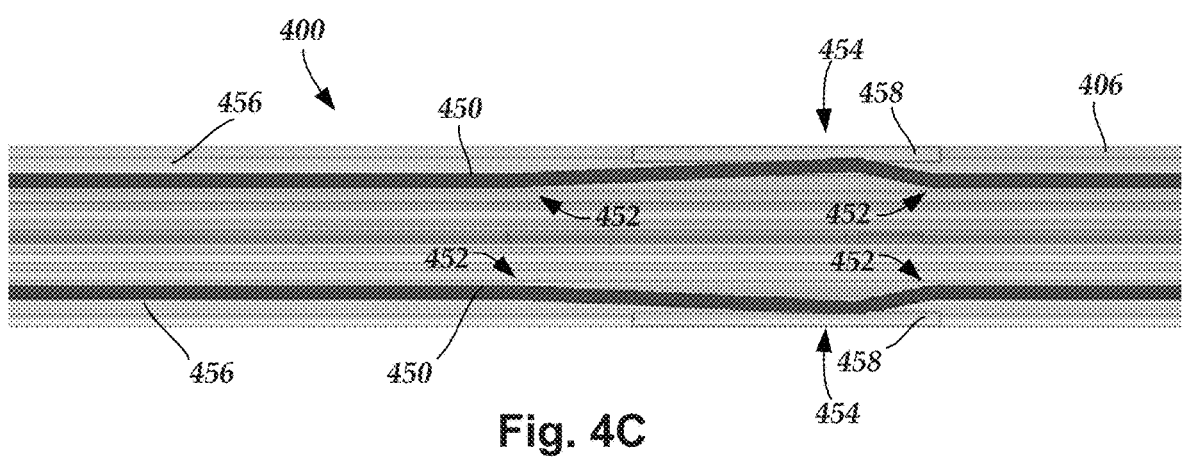
FIG. 4C is a schematic longitudinal cross-sectional view of one embodiment of the multi-lumen guide of the lead of FIG. 4A with the anchoring elements in a constrained position, according to the invention.

In at least some embodiments, each extension portion 454 can be pushed into the lead body 406 through the slot 458 and into the anchoring lumen 456 in a constrained position as illustrated, for example, in FIG. 4C. The constrained position is useful during implantation of the lead to reduce the effective lead diameter to no greater than the inner diameter of an introducer. For example, the introducer (for example, a needle, sheath, cannula, or the like) can push each anchoring element 450 into the constrained position as the lead is loaded into the introducer. When the introducer is removed, the anchoring elements 450 return or attempt to return to the deployed position by extending the extension portion 454 of each anchoring element 450 out of the corresponding slot 458 and into patient tissue.

Each of the anchoring elements 450 has a thin, elongate structure and can be made of, for example, a conductive or non-conductive wire of any suitable length. In at least some embodiments, the anchoring element 450 is made of the same material as electrodes of the lead or can be made of a shape memory or superelastic material such as a Ni—Ti alloy (for example, Nitinol™), or any combination of those materials. In at least some embodiments, the anchoring element 450 is insulated with a covering or coating of at least one non-conductive material.

Any suitable number of anchoring elements 450 can be used. For example, a lead can have 1, 2, 3, 4, 5, 6, 8, 10, 12, 14, 16, or more anchoring elements 450 (or extension portions 454 with fewer anchoring elements 450). In the illustrated embodiment, each anchoring element 450 is in a different anchoring lumen 456, but, in other embodiments, two or more anchoring elements 450 can reside in the same anchoring lumen.

Figure 4D:
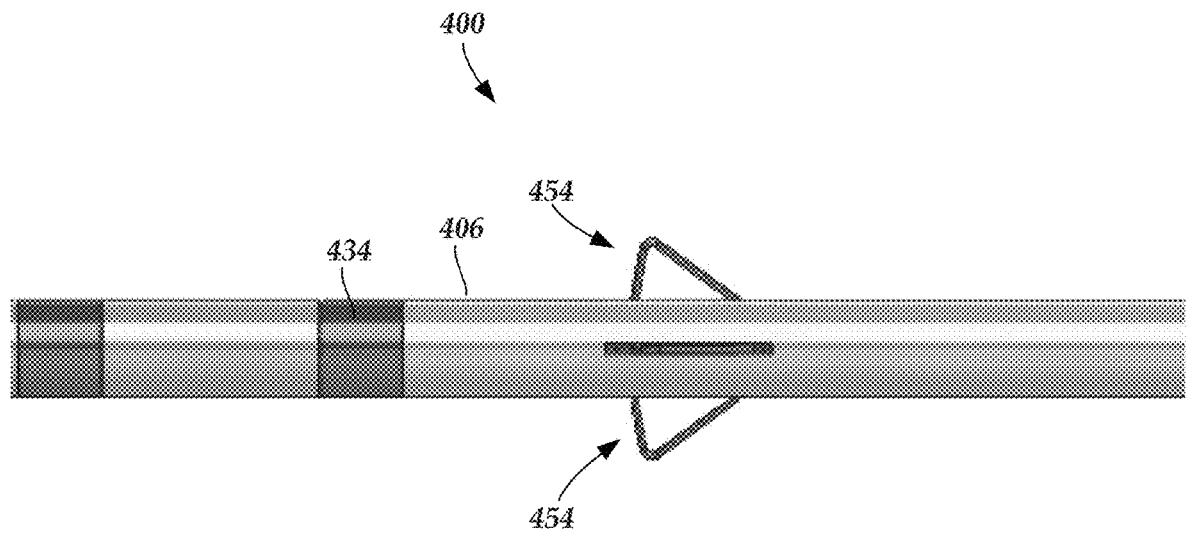
FIG. 4D is a schematic perspective view of a portion of another embodiment of a multi-lumen guide of a lead with anchoring elements, according to the invention.
Figure 4E:
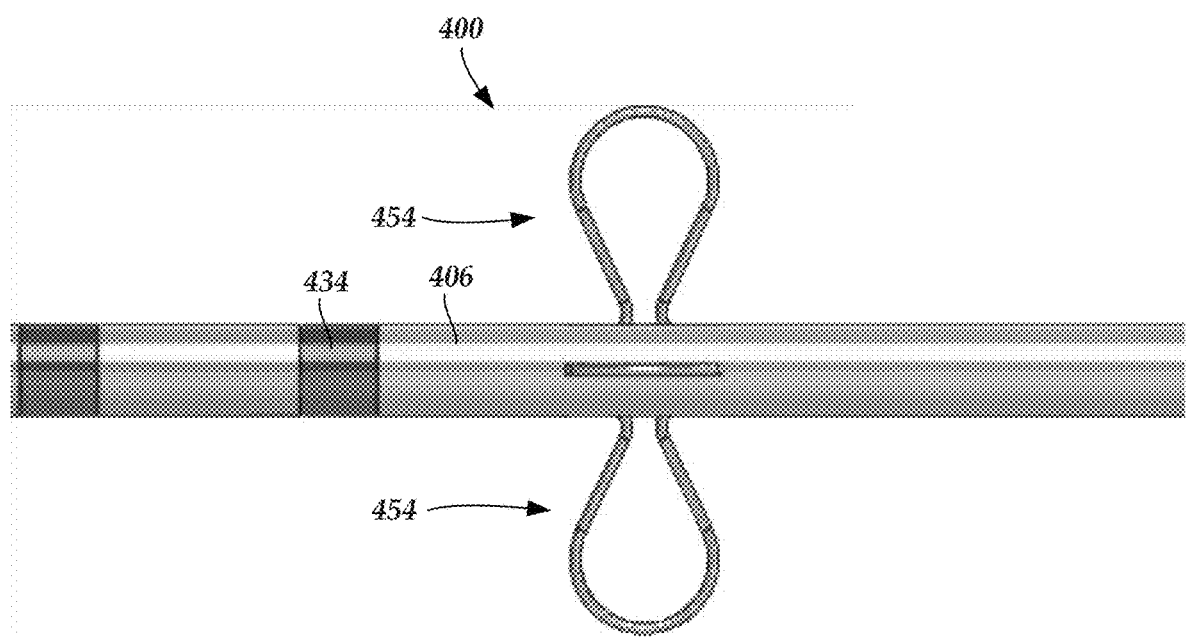
FIG. 4E is a schematic perspective view of a portion of a further embodiment of a multi-lumen guide of a lead with anchoring elements, according to the invention.

Each extension portion 454 may have the same or a different shape. For example, each extension portion 454, in the deployed position, may form two sides (with equal or different lengths) of a triangular shape. In the illustrated embodiment of FIGS. 4A-4C, the distal side of the triangular shape is longer than the proximal side. This triangular shape may facilitate sliding an introducer over the lead body 406 (from the distal end toward the proximal end) and thereby pushing the anchoring element 450 into the constrained position. After implantation, this triangular shape may increase the amount of force necessary to move the lead body 406 relative to the surrounding tissue, especially in the direction where the short side of the triangle pushes against the tissue. In other embodiments, the distal side of the triangular shape is shorter, as illustrated in FIG. 4D. In yet other embodiments, the extension portion 454 forms an arc shape (for example, the arc may curve away from the lead body 406, form an apex, then curve toward the lead body 406), as illustrated in FIG. 4E. Any other suitable shape of the extension portion can be used. In addition, a lead can include any combination of different shapes of the extension portions 454 of the anchoring elements 450. For example, a lead may include one or more anchoring elements 450 with extension portions 454 having the shape illustrated in FIG. 4A and one or anchoring elements 450 with extension portions 454 having the shape illustrated in FIG. 4D. Any other combination of the shapes illustrated in FIGS. 4A-4E can be used.

In the illustrated embodiment, the extension portions 454 are all proximal to the electrodes 434. Other arrangements are possible including one or more extension portions 454 distal to one or more electrodes 434, at least one extension portion 454 positioned laterally between electrodes 434, or any combination thereof. In addition, in some embodiments, the extension portions 454 are nearer the electrodes than the terminals (see, for example, FIGS. 4D and 4E). For example, in some embodiments, the extension portions may be disposed a distance away from the nearest electrode that is within 1, 2, 3, 4, or 5 times the spacing between adjacent electrodes. In some embodiments, the extension portions 454 may be nearer the terminals than the electrodes.

In the illustrated embodiment, each of the extension portions 454 are intermediate the distal and proximal ends of the slots 458. When the anchoring elements 450 are constrained by the introducer, the anchoring elements 450 may extend in the anchoring lumens 456 further toward the distal tip of the lead to accommodate the extension portions 454 within the anchoring lumens.

Figure 4F:
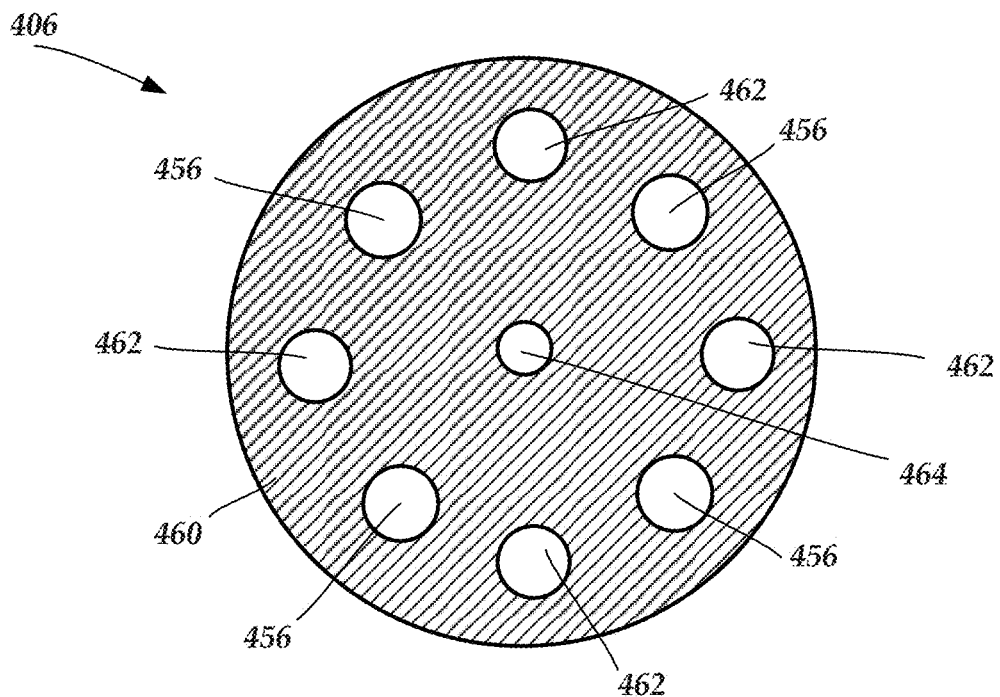
FIG. 4F is a schematic lateral cross-sectional view of one embodiment of the multi-lumen guide of the leads of FIGS. 4A-4E taken at line 4F-4F, according to the invention.
Figure 4G:
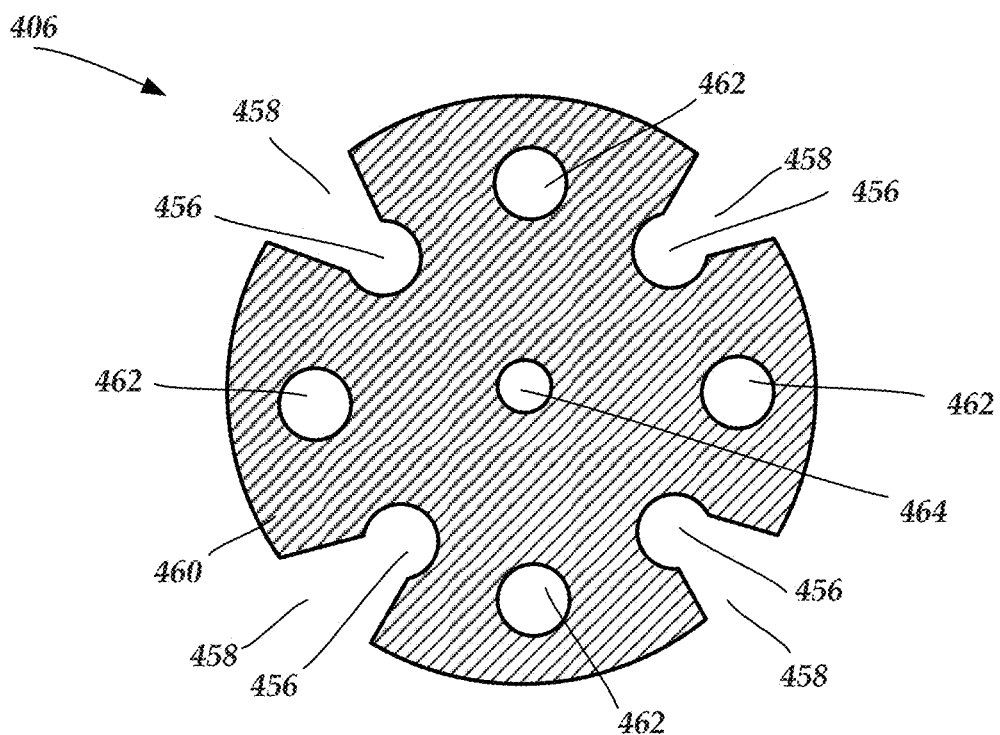
FIG. 4G is a schematic lateral cross-sectional view of one embodiment of the multi-lumen guide of the leads of FIGS. 4A-4E taken at line 4G-4G, according to the invention.

FIG. 4F and FIG. 4G, respectively taken along lines 4F-4F and 4G-4G of FIG. 4A, show one embodiment of the lead body 406, including a multi-lumen guide 460 that defines at least one anchoring lumen 456 and at least one conductor lumen 462. In at least some embodiments, each anchoring lumen 456 carries at least one anchoring element 450, and each conductor lumen 462 carries at least one conductor. In at least some embodiments, a lumen 456, 462 includes both a conductor and an anchoring element 450. In at least some embodiments, an anchoring element 450 in an anchoring lumen 456 is also a conductor that electrically couples a terminal to an electrode. In at least some embodiments, the multi-lumen guide 460 includes a central lumen 464 for a stylet or for passage of drugs or fluids to the treatment site. Optionally, the lead body 406 includes the multi-lumen guide 460 with a jacket (not shown) disposed over the multi-lumen guide, but also includes slots 458 through the corresponding sites on the jacket.

In at least some embodiments, the number of conductor lumens 462 totals 1, 2, 3, 4, 5, 6, 8, 10, 12, 14, 16, or more lumens. In at least some embodiments, the number of anchoring lumens 456 totals 1, 2, 3, 4, 5, 6, 8, or more lumens. The number of conductor lumens 462 may be equal to, fewer than, or more than the number of anchoring lumens 456. In at least some embodiments, each pair of anchoring lumens 456 is separated by at least one conductor lumen 462. In at least some embodiments, each anchoring lumen 456 is smaller than, larger than, or the same size as a conductor lumen 462.

In at least some embodiments, the anchoring lumens 456 (and thereby the anchoring elements 450) may be spaced apart from each other around the lead body 406. In at least some embodiments, the anchoring lumens 456 may be non-uniformly or uniformly spaced apart from each other. In at least some embodiments, the anchoring lumens 456 may be spaced apart from each other by 60°, 90°, 120°, or 180° around the lead body 406, or any combination thereof.

The slots 458 can be formed by any suitable method including, but not limited to, removing a portion of the multi-lumen guide 460, as illustrated in FIG. 4G. The removal of material to form the slots 458 can be performed by any suitable method including, but not limited to, ablation, cutting, grinding, or the like.

Figure 5A:
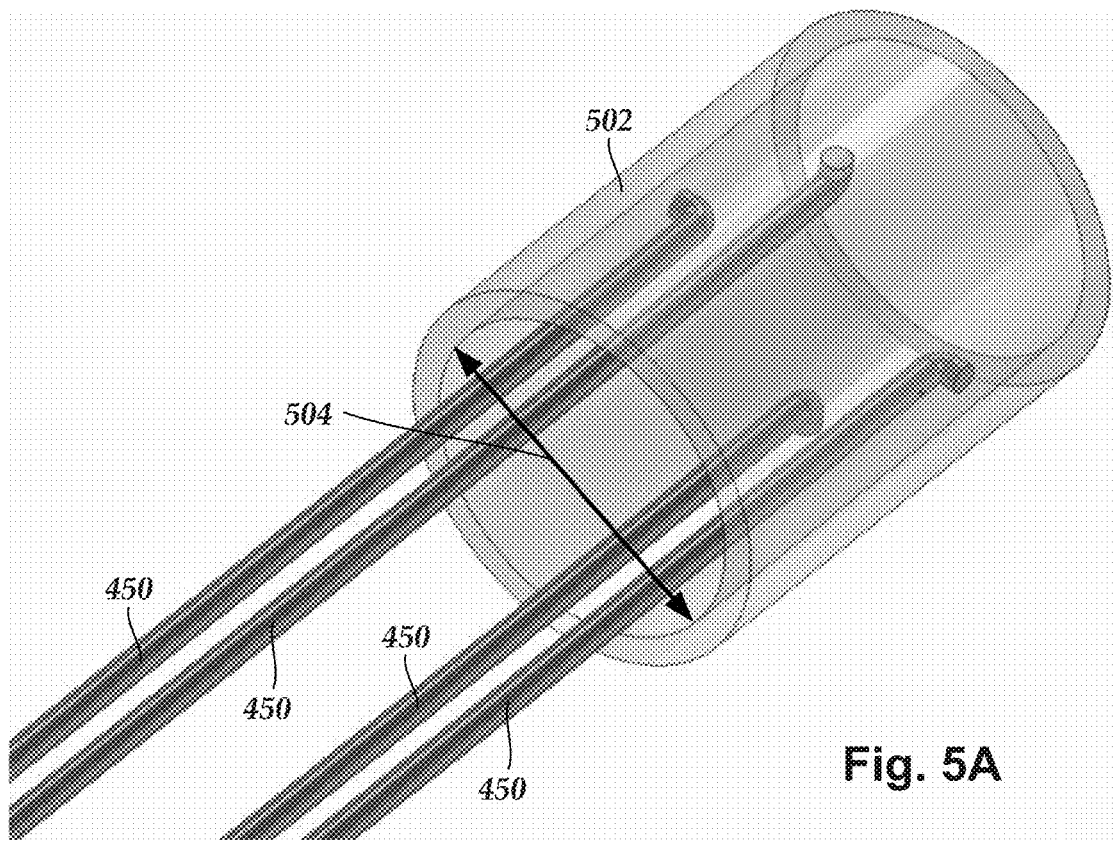
FIG. 5A is a schematic perspective view of one embodiment of an attachment member attached to anchoring elements, according to the invention.

FIG. 5A is a perspective view of an attachment member 502 attached to the anchoring elements 450 (the attachment member 502 is illustrated as partially transparent to show attachment of the anchoring elements 450). The attachment member 502 can have a ring shape or any other suitable shape. In at least some embodiments, the attachment member 502 may also be a marker band, retention sleeve, terminal, contact, or the like. The attachment member 502 can be made of metal, plastic or any other suitable biocompatible material.

In the illustrated embodiment, the attachment member 502 is attached to all of the anchoring elements 450. In at least some other embodiments, the attachment member 502 is attached to less than all of the anchoring elements 450, particularly if the lead includes at least two attachment members 502.

In at least some embodiments, the attachment member 502 is attached to the anchoring elements 450 by welding, soldering, brazing, adhesive, mechanical joints, or the like. The attachment member 502 may be attached to the anchoring elements 450 prior or subsequent to the anchoring elements 502 being disposed in the anchoring lumens 456. The anchoring elements 450 may be shaped (for example, shaping the bent portion 452 or the extension portion 454) prior or subsequent to attaching the anchoring elements 450 to the attachment member 502 (and prior to or subsequent to being disposed in the anchoring lumens 456).

Figure 5B:
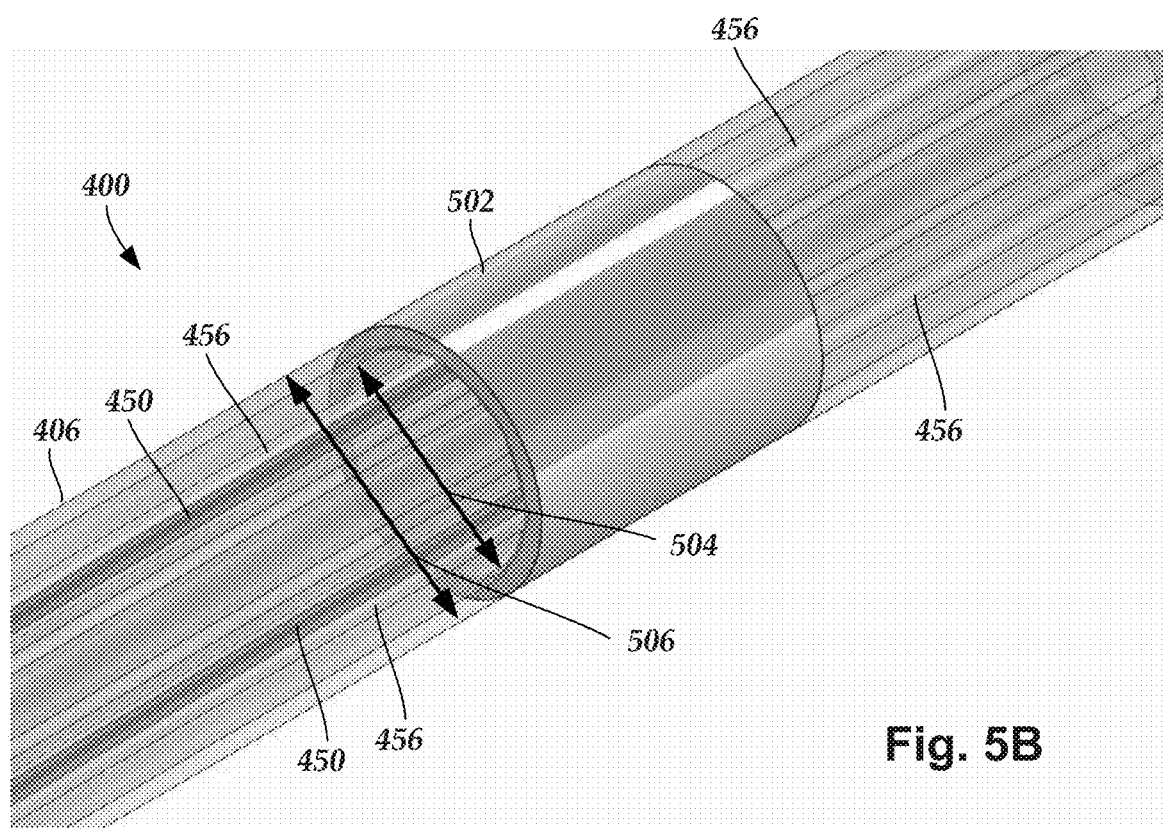
FIG. 5B is a schematic perspective view of the anchoring elements and the attachment member of FIG. 5A applied to the multi-lumen guide of the lead of FIG. 4A, according to the invention.

As shown in FIG. 5B, the attached anchoring elements 450 are disposed in the anchoring lumens 456 while the attachment member 502 is disposed along the lead body 406. The attachment member 502 may be disposed at any suitable position on the lead body 406. In at least some embodiments, the attachment member 502 is disposed proximal to slots 458 (for example, at a position that, prior to explant of the lead, is more accessible than the distal end of the lead body 406, such as proximal to a longitudinal mid-point of the lead).

In the illustrated embodiment, the proximal end portions of the anchoring elements 450 terminate at the attachment member 502. In at least some embodiments, the anchoring lumen 456 terminates at the attachment member 502 (proximal to the attachment member 502 or may extend proximal of the attachment member with the anchoring lumen 456 and, at least in some embodiments, this proximal portion being filled with polymer material prior to or after insertion of the anchoring element 450 into the anchoring lumen 456).

In at least some embodiments, the attachment member 502 can be disposed on the lead body 406 using a method similar to disposition of the electrodes or terminals or can be disposed on the lead by sliding onto the lead, swaging, adhesive attachment, or the like.

Figure 5C:
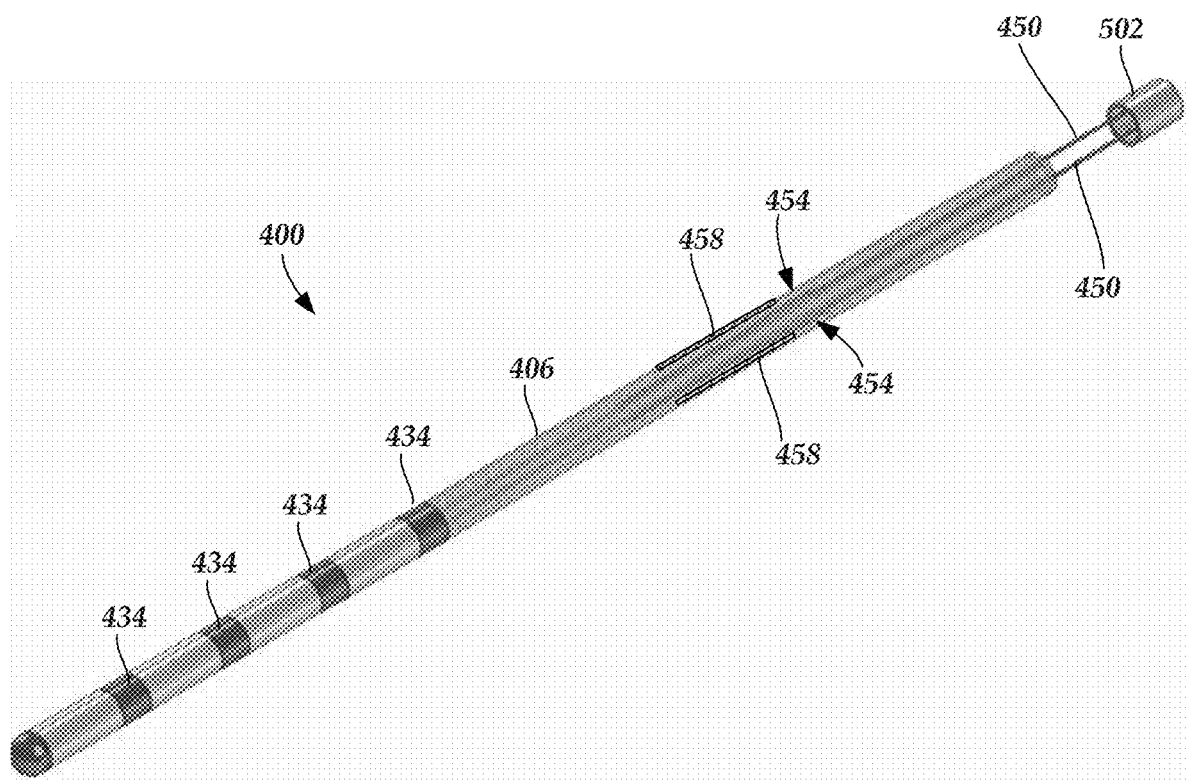
FIG. 5C is a schematic perspective view of the anchoring elements and the attachment member of FIG. 5A moved relative to the multi-lumen guide of the lead of FIG. 4A to retract the anchoring elements, according to the invention.

In at least some embodiments, the attachment member 502 can be used to pull the attached anchoring elements 450 into a restrained position, for example, as illustrated in FIG. 5C. In the illustrated embodiment of FIG. 5C, the lead 400 is prepared for explantation by cutting away the portion of the lead body proximal to the attachment member 502 so that the attachment member can be detached from the lead body 406. In the illustrated embodiment, the extension portions 454 in the restrained position are proximal to the corresponding slots 458. In at least some embodiments, moving the attachment member 502 along the lead body 406 (or partially or completely off the lead body 406) retracts the anchoring elements 450 into the restrained position. Retracting the anchoring elements 450 can be useful to reduce the overall diameter of the lead for explanting the lead. In at least some embodiments, the attachment member 502 can be moved to completely remove the anchoring elements 450 from the lead body 406 prior to explanting the lead.

In at least some embodiments, one or more of the anchoring elements 450 can each be attached to an electrode 434 with a connection that is weaker than the attachment to the attachment member 502. In this case, for example, when the attachment member 502 is pulled with sufficient force, the connection with the electrode 434 may break so that the anchoring members 502 can be removed from the lead. In at least some of these embodiments, one or more of the anchoring elements 450 can also act as a conductor electrically coupling a terminal to an electrode.

In at least some embodiments, the attachment member 502 can be pulled by hand or with a tool, such as, for example, forceps, tweezers, or the like. To facilitate movement of the attachment member 502, the lead body 406 can be cut near the attachment member 502 (for example, proximal to the attachment member 502, such as along the proximal edge of the attachment member 502).

Figure 6A:
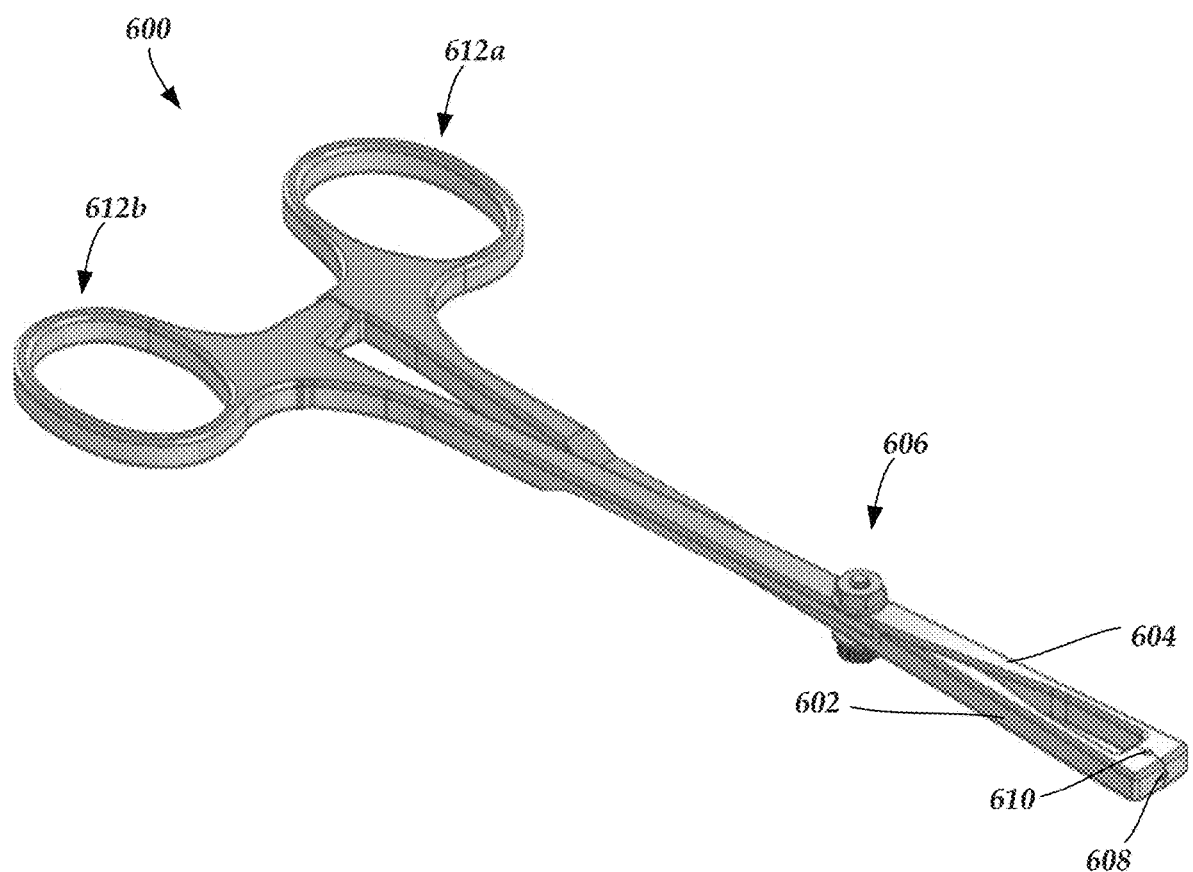
FIG. 6A is a schematic perspective view of one embodiment of a retraction tool, according to the invention.

FIG. 6A illustrates one embodiment of a tool 600 that can be used to pull the attachment member 502. The tool 600 has two members 602, 604 that pivot relative to each other about a hinge 606 (for example, a pivot hinge, spring hinge, or any other suitable hinge). In the closed position, the hinged members 602, 604 form two apertures 608, 610 or only one of the apertures 608, 610.

Each of the apertures 608, 610 may have an inner diameter that is less than the outer diameter of the attachment member 502 to push or pull the attachment member when the aperture 608 or 610 is closed around and slid along the lead body 406. The inner diameter may also be less than the outer diameter of the lead body 406 to compress the lead body 406. Compressing the lead body 406 near the attachment member 502 (for example, distal or proximal, or both, to the attachment member 502) can be useful to reduce the amount of friction between the lead body 406 and the attachment member 502. In at least some embodiments, the inner diameters of the apertures 608, 610 are different sizes to accommodate different sizes of lead bodies or attachment members.

In at least some embodiments, the tool 600 includes gripping members 612a, 612b (for example, finger rings, finger tangs, cross-hatched or serrated surfaces, or any other suitable gripping members or any combination thereof). The gripping members 612a, 612b may be opposite the hinge 606 from the apertures 608, 610 (for example, when employing a pivot hinge) or may be on the same side as the apertures 608, 610 (for example, when employing a spring hinge).

In at least some embodiments, the hinged members 602, 604 terminate at or about the hinge 606. In at least some embodiments, the hinged members 602, 604 are biased to the open or closed position (for example, biased by a spring, elastic band, or the like). In other embodiments, the hinged members are not biased to either position. The tool 600 may be locking or non-locking. In some embodiments, the hinged members 602, 604 may each include interlocking teeth that engage each other in the closed position. The tool 600 may be made of plastic, rubber, metal, or any other suitable material or any combination thereof.

Figure 6B:
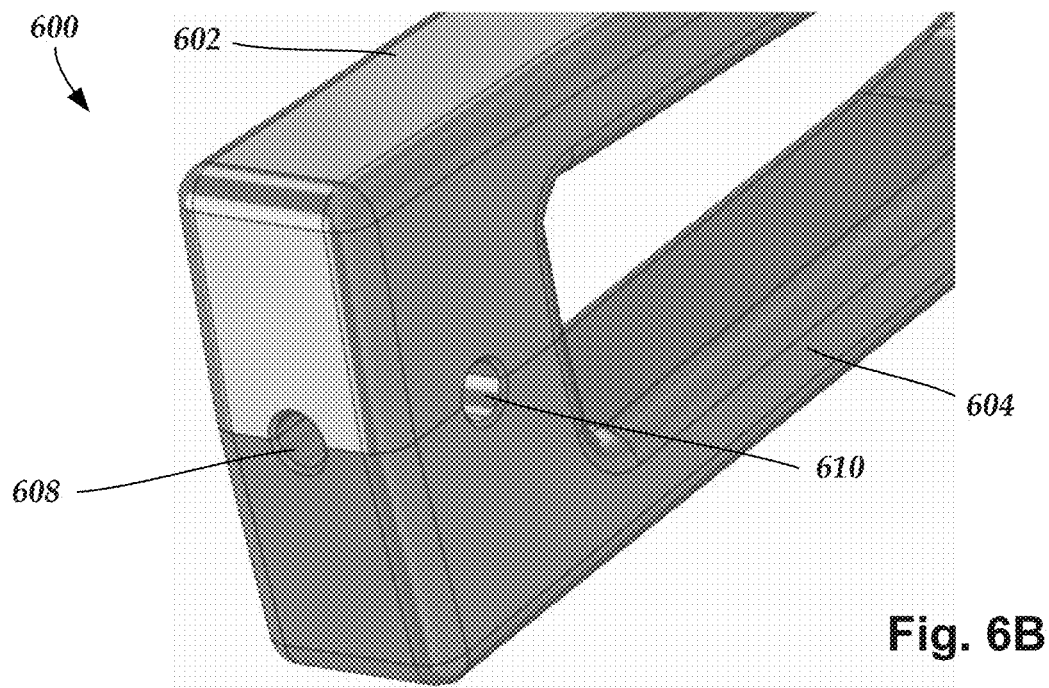
FIG. 6B is a schematic perspective view of the retraction tool of FIG. 6A in a closed position, according to the invention.

FIG. 6B is a close-up view of the apertures 608, 610. In at least some embodiments, at least one of the apertures 608, 610 has at least one counterbore that slidingly catches the attachment member 502 while the aperture 608 or 610 compresses the lead body 406 (for example, as shown in FIG. 6D). In at least some embodiments, at least one of the apertures 606, 608 has two opposing counterbores (for example, as shown in FIG. 6D), one to pull the attachment member 502 and another to push the attachment member 502. The inner diameter of each counterbore may be larger than the outer diameter of the attachment member 502. Alternatively to a counterbore, at least one of the apertures 608, 610 may include a countersink.

Figure 6C:
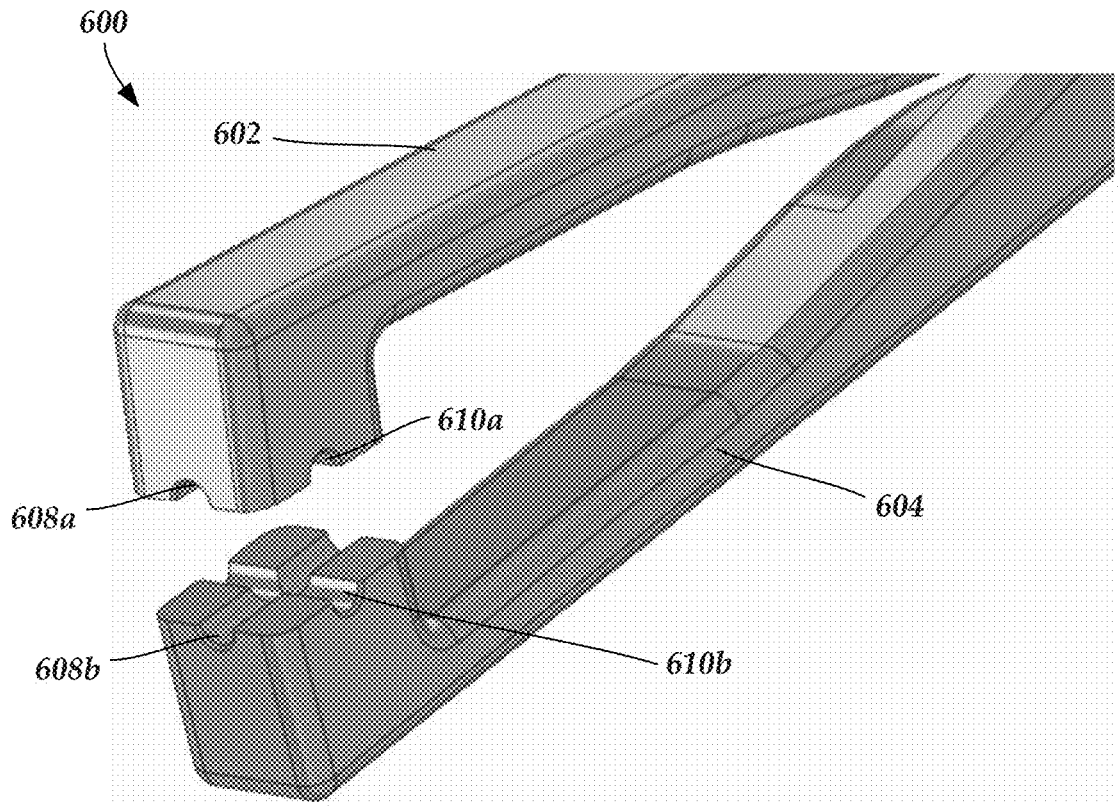
FIG. 6C is a schematic perspective view of the retraction tool of FIG. 6A in an open position, according to the invention.
Figure 6D:
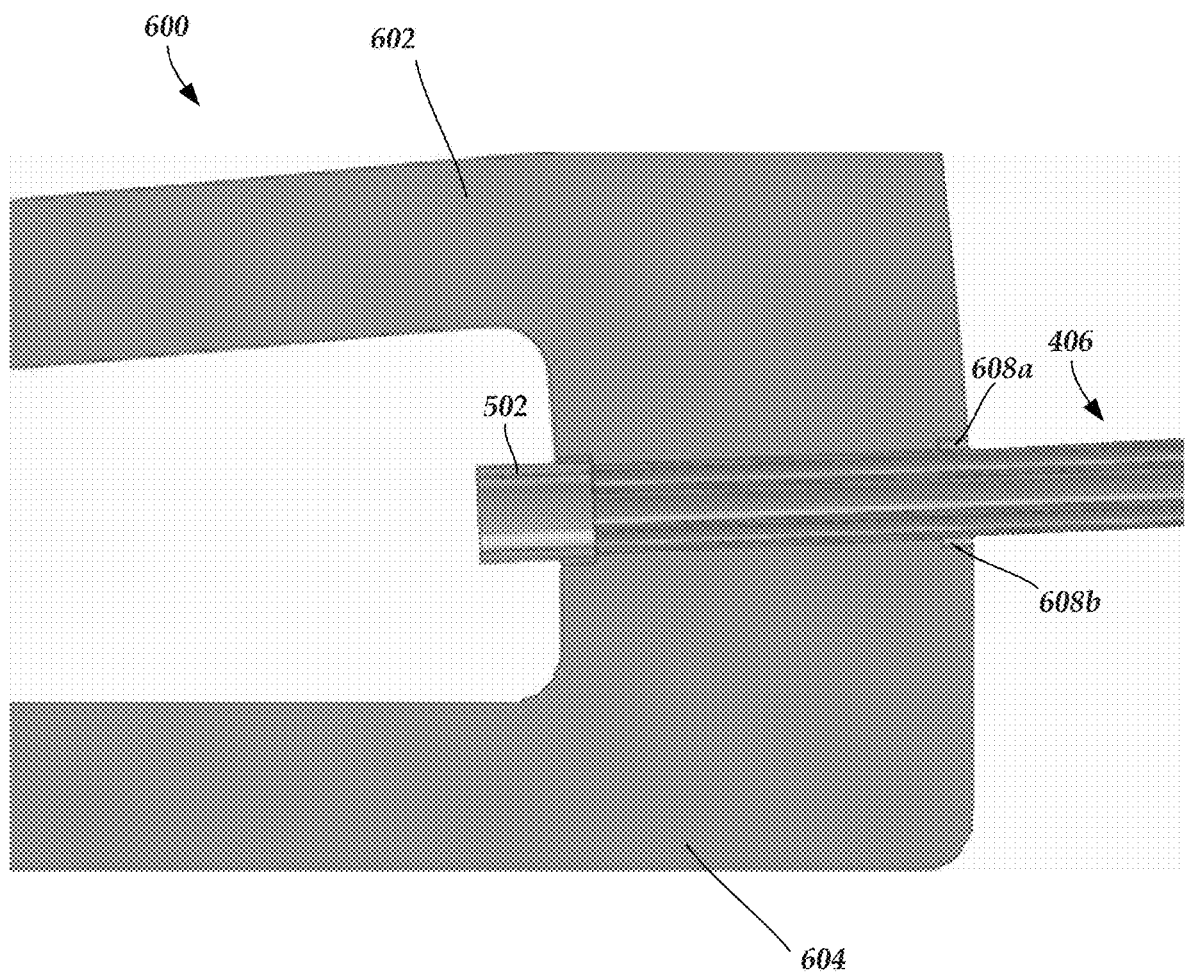
FIG. 6D is a schematic cross-sectional side view of the retraction tool of FIG. 6A used to move the attachment member of FIG. 5A relative to the multi-lumen tube of the lead of FIG. 4A, according to the invention.

As shown in FIG. 6C, one hinged member 602 may define a first portion of each aperture 608a, 610a while the other hinged member 604 defines a second portion of each aperture 608b, 610b. At least one of the first portions 608a, 610a may be symmetrical or asymmetrical to the corresponding second portion 608b or 610b. In the illustrated embodiment, the aperture 608 permits sliding the attachment member 502 parallel to the longitudinal axis of the tool 600 (as shown in FIG. 6D), whereas the aperture 610 permits sliding the attachment member 502 perpendicular to the longitudinal axis of the tool 600.

When the attachment member 502 is engaged by the tool 600, the attachment member 502 can be pulled away from a remainder of the lead to separate the attachment member 502 and attachment elements 450 from the lead. This then retractions the extension portions 454 into (and optionally out of the lead) so that they no longer engage tissue and allow the lead to be more easily explanted. It will be understood that other tools, such as forceps or specially-designed tools, can be used to pull the attachment member 502 and attachment elements 450 away from the lead to facilitate explantation of the lead.

Figure 7:
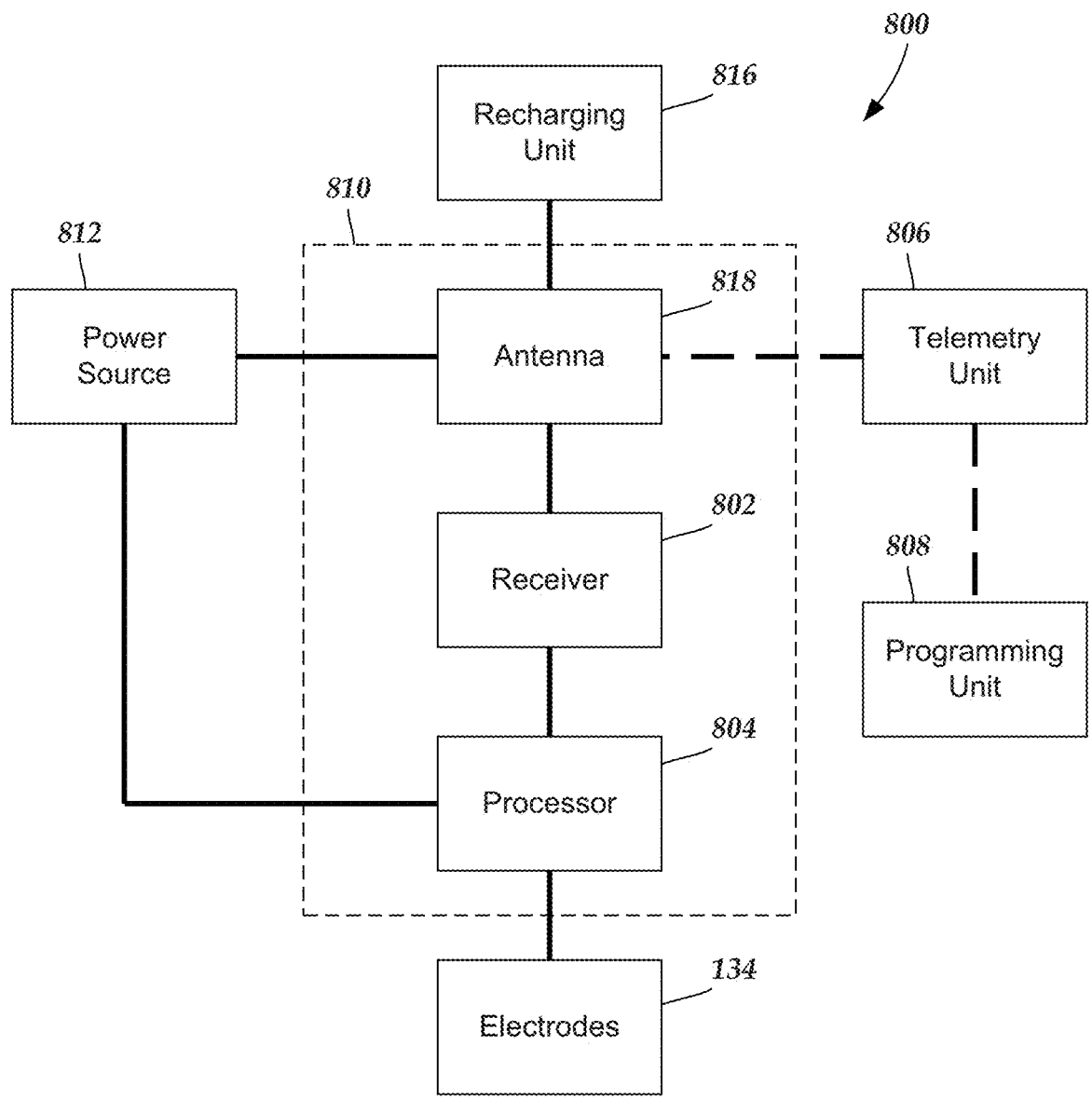
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on at least one circuit board or similar carrier within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control at least one of the timing, frequency, strength, duration, and waveform of the pulses. In addition, the processor 704 can select which electrodes can be used to provide stimulation, if desired. In at least some embodiments, the processor 704 selects which electrode(s) are cathodes and which electrode(s) are anodes. In at least some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (for example, RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying at least one of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body comprising a distal end portion, a proximal end portion, and a longitudinal length, wherein the lead body further comprises at least one anchoring lumen that extends longitudinally along at least a portion of the lead body, wherein the lead body further comprises at least one open slot that is spaced apart from each end of the lead body, wherein each of the at least one anchoring lumen is open at one of the at least one open slot and extends both distally and proximally from the one of the at least one open slot;
   a plurality of electrodes disposed along the distal end portion of the lead body;

a plurality of terminals disposed along the proximal end portion of the lead body;

a plurality of conductors electrically coupling the terminals to the electrodes;

at least one anchoring element at least partially disposed in one of the at least one anchoring lumen, wherein each of the at least one anchoring element comprises at least one bent portion that is biased to extend an extension portion of the anchoring element out of one of the at least one slot when the anchoring element is in a deployed position and can retract the extension portion into the respective anchoring lumen when the anchoring element is in a constrained position; and an attachment member attached to each of the at least one anchoring element, wherein the attachment member is disposed proximal to each of the at least one slot, wherein the attachment member is a band disposed along the lead body.

2. The electrical stimulation lead of claim 1, wherein the lead body has an outer diameter that exceeds an inner diameter of the band.

3. The electrical stimulation lead of claim 1, wherein the attachment member comprises at least two separate attachment members and the at least one anchoring element comprises a plurality of anchoring elements, each of the at least two separate attachment members being attached to different ones of the anchoring elements.

4. The electrical stimulation lead of claim 1, wherein the at least one anchoring element comprises a plurality of anchoring elements, the anchoring elements being spaced apart from each other around the lead.

5. The electrical stimulation lead of claim 4, wherein the anchoring elements are uniformly spaced apart from each other around the electrical stimulation lead.

6. The electrical stimulation lead of claim 4, wherein the anchoring elements are non-uniformly spaced apart from each other around the electrical stimulation lead.

7. The electrical stimulation lead of claim 4, wherein the extension portions of at last two of the anchoring elements have different shapes.

8. The electrical stimulation lead of claim 1, wherein, when the extension portion of one of the at least one anchoring element extends out of the slot associated with the anchoring element, the extension portion forms two sides of a triangular shape that extends away from the lead body.

9. The electrical stimulation lead of claim 8, wherein the two sides of the triangular shape include a distal side and a proximal side, the proximal side being shorter than the distal side.

10. The electrical stimulation lead of claim 8, wherein the two sides of the triangular shape include a distal side and a proximal side, the distal side being shorter than the proximal side.

11. The electrical stimulation lead of claim 1, wherein, when the extension portion of one of the at least one anchoring element extends out of the slot associated with the one anchoring element, the extension portion has an arc shape.

12. The electrical stimulation lead of claim 1, wherein each of the at least one anchoring element is attached to at least one of the plurality of electrodes.

13. An electrical stimulating system, comprising:
the electrical stimulation lead of claim 1; and
a control module coupleable to the electrical stimulation lead.

14. A method of implanting the electrical stimulation lead of claim 1, the method comprising:
sliding an introducer over the lead body to push each of the at least one anchoring element through the slot associated with the anchoring element into the constrained position in the anchoring lumen in which the anchoring element is disposed;
implanting the electrical stimulation lead into tissue of a patient while the introducer constrains each of the at least one anchoring element in the constrained position; and
removing the introducer to extend each of the at least one anchoring element from the constrained position to the deployed position in the tissue of the patient.

15. A method of explanting the electrical stimulation lead of claim 1, the method comprising:
pulling the attachment member in a direction away from the at least one slot, thereby retracting each extension portion of each of the at least one anchoring element through the slot associated with the anchoring element into the anchoring lumen in which the anchoring element is disposed; and
explanting the lead body from tissue of a patient after pulling the attachment member.

16. The method of claim 15, further comprising:
prior to pulling the attachment member, cutting the lead body proximal to the attachment member so that the attachment member can be disengaged from the lead body.

17. The method of claim 15, further comprising:
while pulling the attachment member, compressing a portion of the lead body distal to the attachment member.

18. The method of claim 15, wherein pulling the attachment member in the direction away from the at least one slot comprises completely removing each of the at least one anchoring element from the lead body.

19. The method of claim 15, wherein explanting the lead body from the tissue of the patient after pulling the attachment member comprises explanting the lead body from the tissue of the patient while each of the at least one anchoring element is at least partially disposed in the lead body in a restrained position and each extension portion of each of the at least one anchoring element is retracted into the anchoring lumen in which the anchoring element is disposed.

* * * * *